US00PP35069P2

(12) United States Plant Patent
Zanetti

(10) Patent No.: US PP35,069 P2
(45) Date of Patent: Mar. 28, 2023

(54) APPLE TREE NAMED 'NICORED'

(50) Latin Name: *Malus domestica*
Varietal Denomination: Nicored

(71) Applicant: Werner Zanetti, Eppan an der Weinstraße (IT)

(72) Inventor: Werner Zanetti, Eppan an der Weinstraße (IT)

(73) Assignee: Werner Zanetti, Eppan an der Weinstraße (IT)

( * ) Notice: Subject to any disclaimer, the term of this patent is extended or adjusted under 35 U.S.C. 154(b) by 0 days.

(21) Appl. No.: 17/890,167

(22) Filed: Aug. 17, 2022

(51) Int. Cl.
*A01H 6/74* (2018.01)
*A01H 5/08* (2018.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Morrison & Foerster LLP

(57) ABSTRACT

A new and distinctive variety of a *Malus domestica* Borkh. apple tree named 'Nicored', particularly characterized by its improved fruit color relative to its parent 'Nicoter', is disclosed.

9 Drawing Sheets

Latin name: Botanical classification: *Malus domestica* Borkh.

Varietal denomination: The varietal denomination of the claimed apple tree variety is 'Nicored'.

BACKGROUND OF THE INVENTION

Apples are an economically important crop. Accordingly, there exists a need to develop new varieties of apple tree with improved characteristics, such as fruit appearance and quality.

BRIEF SUMMARY OF THE INVENTION

In order to meet these needs, the present invention is directed to an improved variety of apple tree. In particular, the invention relates to a new and distinct variety of apple tree (*Malus domestica* Borkh.), which has been denominated as 'Nicored'.

The present variety 'Nicored' was discovered in September 2010 as an improved color strain/mutation on a standard 'Nicoter' (U.S. Plant Pat. No. 17,201) tree that was present in the Applicant's orchard in Eppan an der Weinstraße, Italy. This mutant tree was observed again in 2011 to evaluate the stability of the improved fruit color phenotype relative to the parent/source 'Nicoter' tree.

Asexual reproduction of the 'Nicored' apple tree variety, which took place in Laimburg, Italy in August 2011 by grafting of one-year-old scions onto M9T337 rootstock, shows that the foregoing and all other characteristics and distinctions are true to type and are established and transmitted through succeeding asexual propagations.

BRIEF DESCRIPTION OF THE DRAWINGS

The 'Nicored' apple tree variety is illustrated by the accompanying photographs which show various morphological features of the tree. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone.

DETAILED BOTANICAL DESCRIPTION

Figure 1:
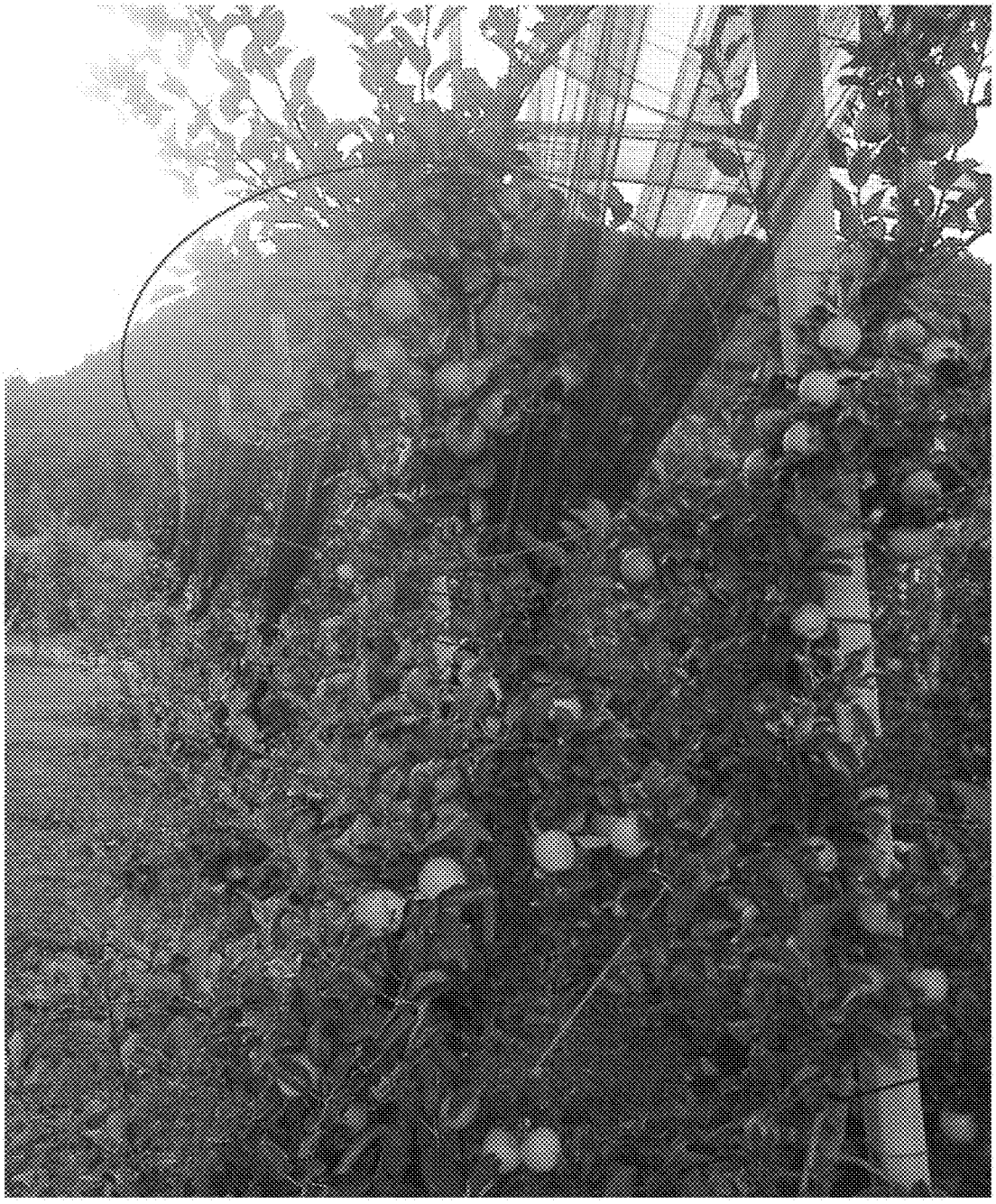
FIG. 1 illustrates the seven-year-old 'Nicoter' source mother tree and the mutated branch of this tree ('Nicored') is shown in the red circle.
Figure 2:
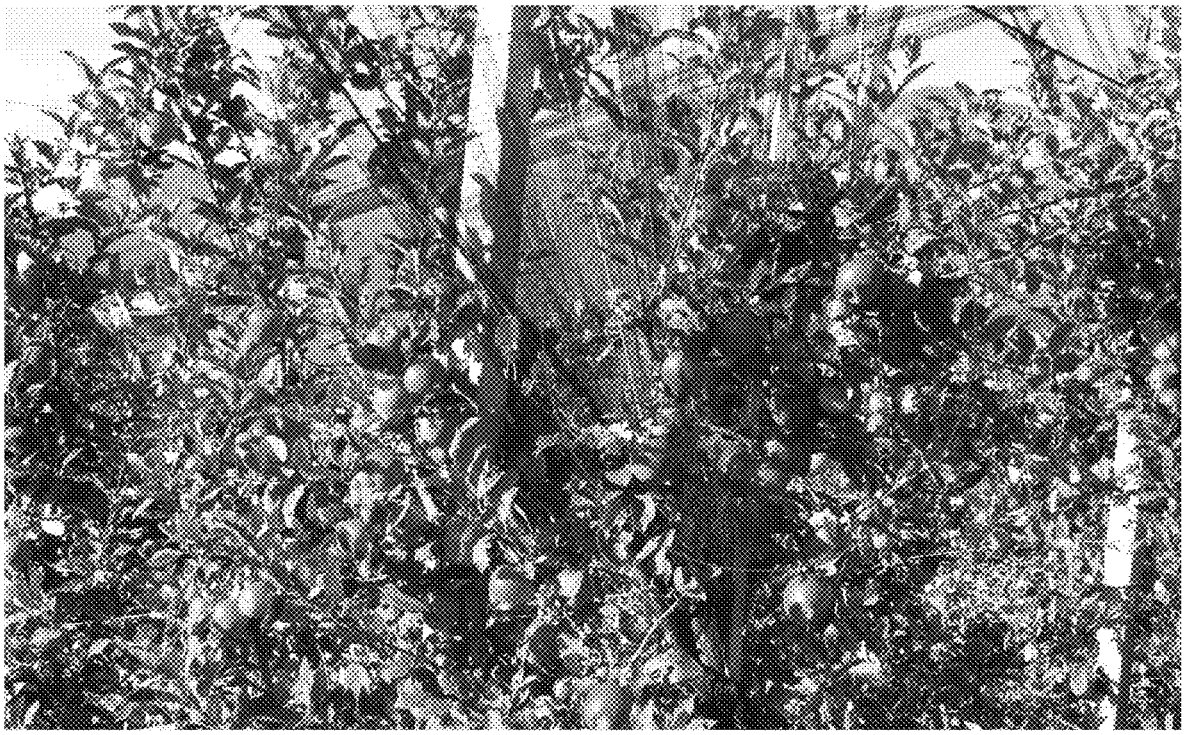
FIG. 2 illustrates the seven-year-old 'Nicoter' source mother tree (right-hand side) and the mutated branch of this tree ('Nicored') is shown in the red circle. On the left-hand side are trees of 'Nicoter'. The trees shown are shortly before harvest.
Figure 3:
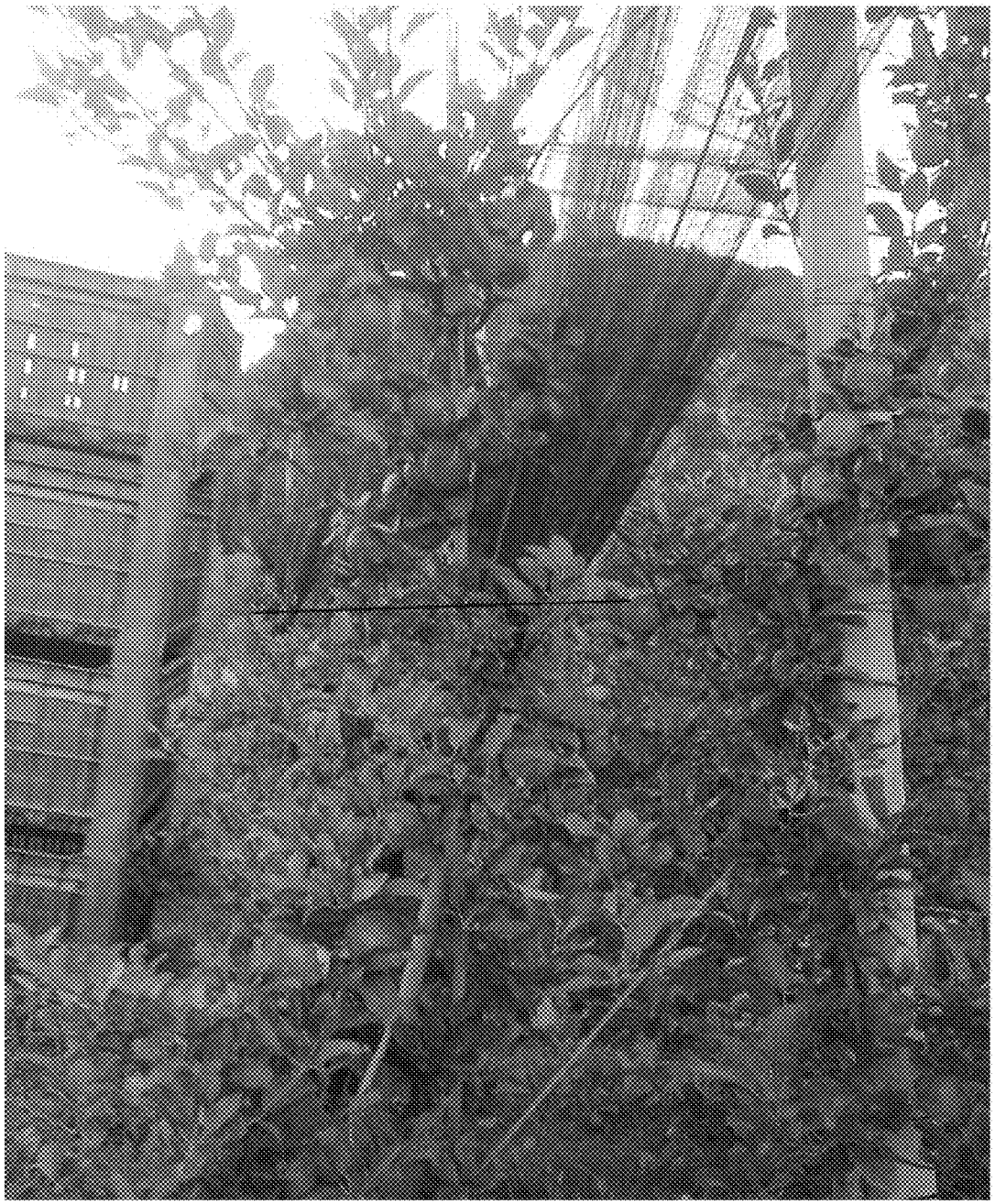
FIG. 3 illustrates the seven-year-old 'Nicoter' source mother tree at harvest and the mutated branch of this tree ('Nicored') is shown above the black horizontal line.
Figure 4:
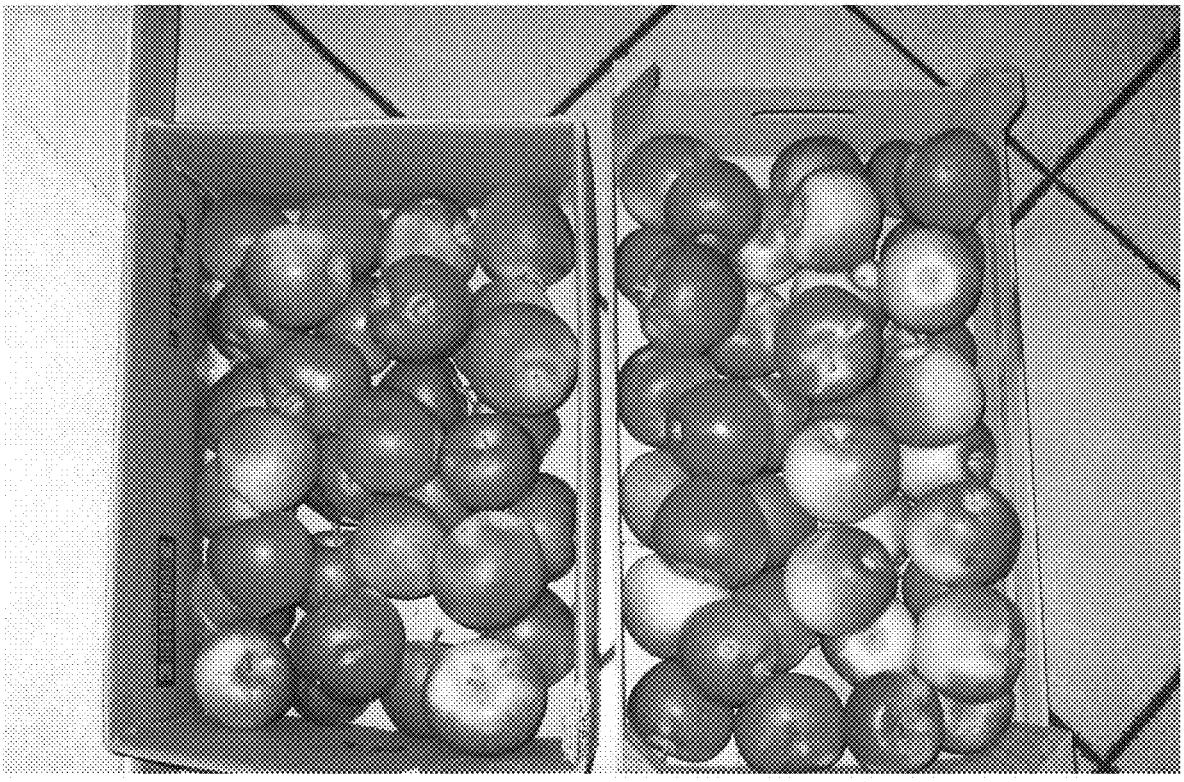
FIG. 4 illustrates fruit from 'Nicored' (left box) and fruit from 'Nicoter' (right box) harvested from the seven-year-old 'Nicoter' source mother tree having the 'Nicored' mutation.
Figure 5:
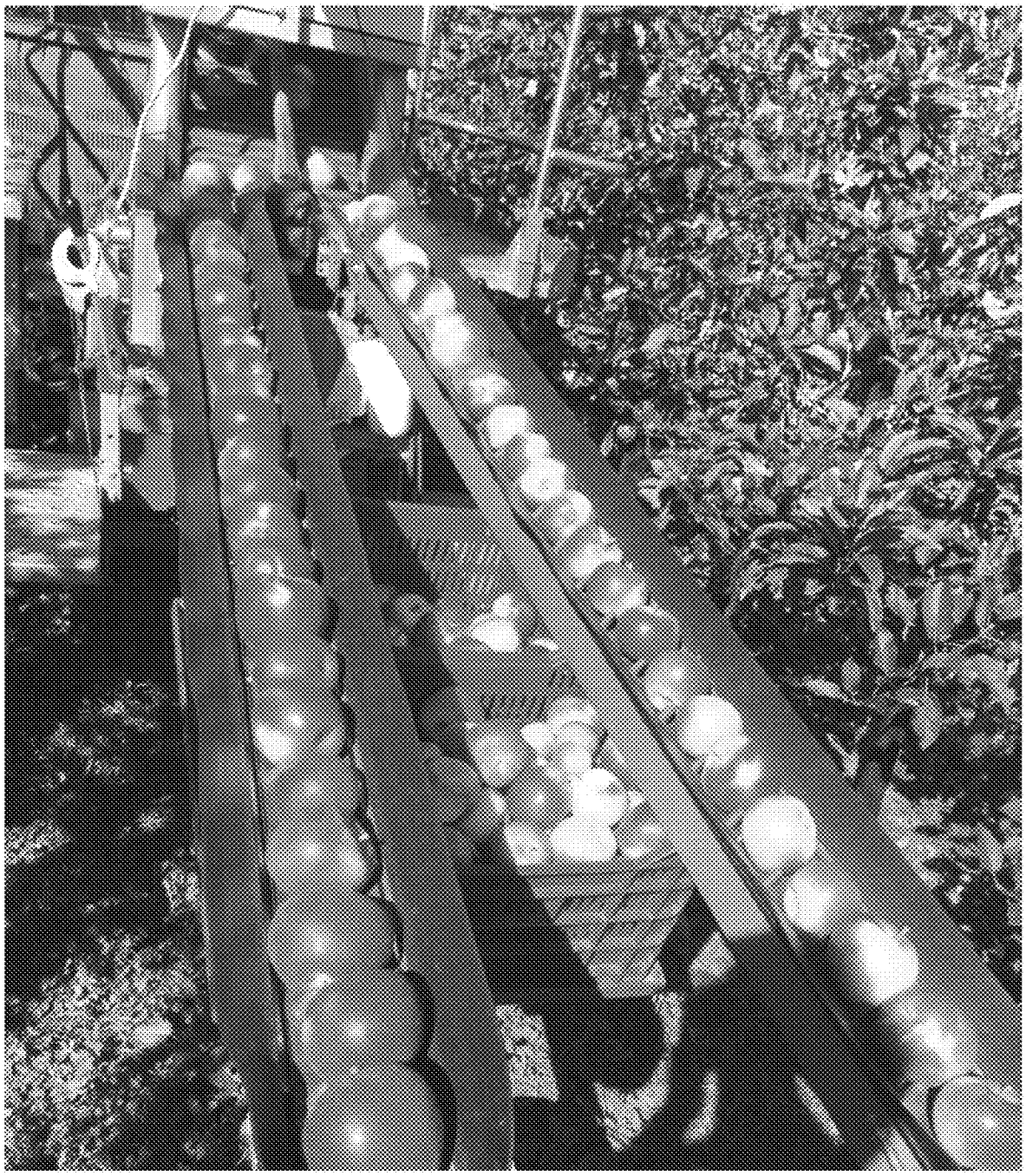
FIG. 5 illustrates fruit of 'Nicored' (left side) next to fruit of the source variety 'Nicoter' (right side). Harvested fruit were photographed in September 2016 in Eppan (Bozer).
Figure 6:
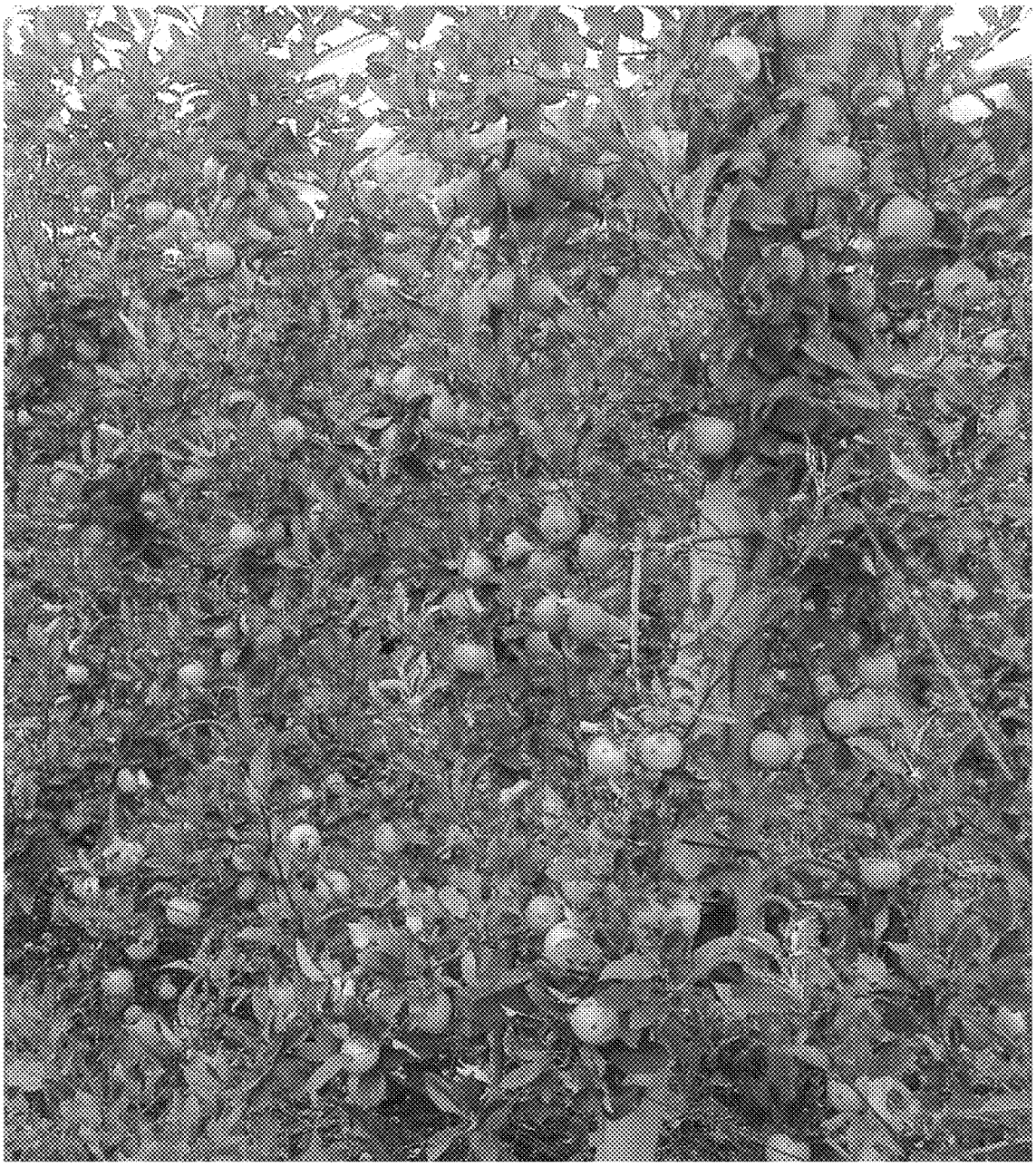
FIG. 6 illustrates a grafted shoot of 'Nicored' with fruit (red circle) grafted onto the source variety 'Nicoter'.
Figure 7:
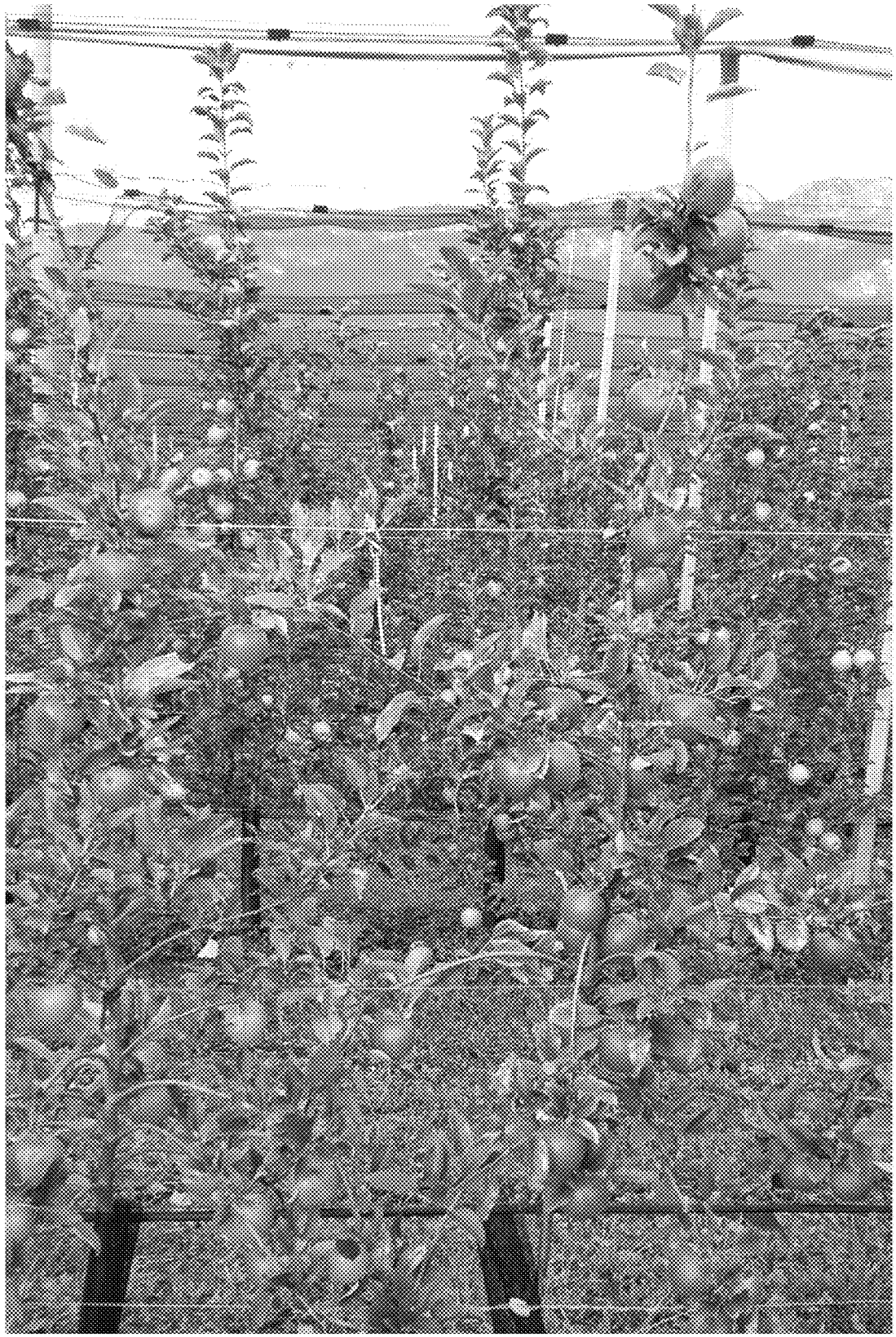
FIG. 7 illustrates the source tree 'Nicoter' (left tree) and mutant tree 'Nicored' (right tree). Trees were two-years-old and were photographed in August 2019 in Kaiserau (Bozen).
Figure 8:
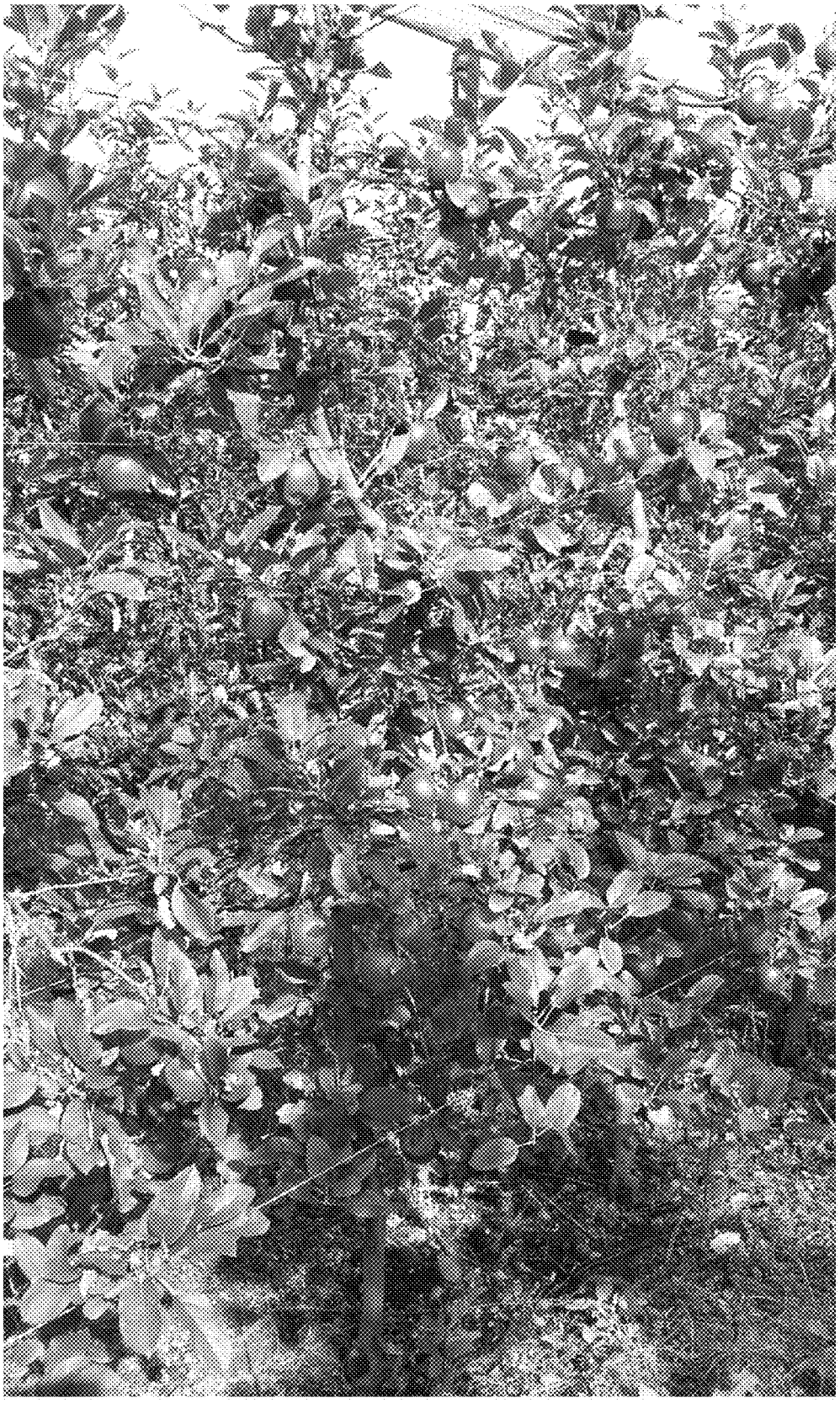
FIG. 8 illustrates a six-year-old 'Nicored' tree.

The following description sets forth the distinctive characteristics of 'Nicored'. The following botanical description of 'Nicored' is based on observations of the originally identified tree, and asexually reproduced progeny. Unless otherwise indicated, the descriptions are from trees that are four (4)-years old grown at a test location in Geldermalsen, The Netherlands.

Certain characteristics, as well as the phenotype, of this variety may vary with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. All color references are from The RHS Colour Chart of The Royal Horticultural Society of London (RHS) (Sixth Edition, 2015).

Tree:

*Type.*—Ramified.

*Tree habit.*—Spreading.

*Vigor.*—Medium.

*Height.*—Approximately 3.00 m.

*Width.*—Approximately 1.00 m.

*Caliper.*—Approximately 35 mm on average at 500 mm above the graft union in 4-year-old trees on M9 T337 rootstock.

*Trunk bark texture.*—Smooth.

*Trunk bark color.*—RHS N200B (Brown).

*Primary branches.*—Spreading; branches emerge at an angle of approximately 10 to approximately 30 degrees, with branches higher in the tree emerging at approximately 30 degrees. Trees are planted as a 2-year-old tree from the nursery with site feathers. The typical and observed lateral branch length is 50 cm (first primary branch above the graft union and arising from the main stem).

*Branch color.*—One-year old branches are RHS 200D (Brown), while older branches are RHS 200B (Brown).

*Branch pubescence.*—Absent.

*Branch lenticels.*—Approximately 3-4 per square cm. Shape: round and elongated. Color: RHS 198C (Greyed-green). Size: Approximately 1 mm long by approximately 1.5 mm wide.

*Branch surface texture.*—Relatively smooth.

*Internodes.*—Average internode length is approximately 4 cm for a 1-year-old shoot.

*Bearing.*—On spurs.

*Hardiness.*—US zone 5.

Leaves:

*Texture.*—Upper surface: smooth. Lower surface: with upright leaf veins.

*Pubescence.*—Upper surface: not present. Lower surface: slightly hairy.

*Sheen.*—Shiny.

*Length.*—104 mm.

*Width.*—66 mm.

*Margin.*—Irregular, every 2-3 mm, more sharp than round.

*Tip (apex) surface.*—More sharp than round.

*Stipules.*—Relatively wide. Length: Average 15 mm. Width: Average 3 mm at base.

*Upper surface texture.*—Slightly hairy. Lower surface texture: slightly hairy. Apex shape: obtuse. Base shape: truncate.

*Leaf color.*—Upper surface: RHS 137A (Green). Lower surface: RHS 138B (Green).

*Leaf vein color.*—RHS 138C (Green).

*Petiole length.*—30 mm.

Flower:

*General.*—Size: 13.48 mm +/− 1.81 mm. Diameter: Approximately 38.57 mm +/− 6.47 mm when fully flattened. Shape: Radially symmetrical-rotate (actinomorphic).

*Flower bud.*—Shape: Obtuse. Color: Unopened bud: RHS 178B (Greyed-red). Opened bud: RHS N144A (Yellow-green).

*Petals.*—Number: 5 per flower. Length: 22.99 mm +/− 1.68 mm. Width: 13.48 mm +/− 1.81 mm. Shape: obovate. Base: truncate/cylindrical waisted. Apex: obtuse. Arrangement: Free/touching. Petal color determined on an open flower: Upper petal surface: RHS N155B (White) to RHS 63B (Red-purple). Lower petal surface: RHS N115B (White) to RHS 63B (Red-purple)(Veins). Petal color determined at balloon stage: RHS 63B (Red-purple).

*Sepals.*—Number: About 5 per flower. Shape: cordate. Apex: acuminate. Base: broad. Length: 7.49 mm +/− 1.21 mm. Width: 4.44 mm +/− 0.55 mm. Color: RHS 143B (Green). Arrangement: Free.

*Pedicel/peduncle.*—Apples do not have branched inflorescences, and hence do not have pedicels. The flower stalk of an apple is the peduncle. Length: Approximately 16 mm. Diameter: Approximately 2 mm. Color: RHS N144A (Yellow-green).

*Stamen.*—Number: Approximately 16-18 per flower. Position of anthers is above the stigmas, didynamous. Length: 8.22 mm +/− 1.72 mm. Filament color: RHS 155C (White).

*Anthers.*—Number: About 16 per flower. Color: RHS 155B (White). Unopened anther color: RHS 4D (Yellow). Pollen color: RHS 4C (Yellow).

*Pistil.*—General: located in the middle of the flower with 5 styles. Length: 12.12 mm +/− 1.16 mm. Number: Typically 5 pistils per flower. Arrangement in flower: Radial. Color: RHS 151C (Yellow-green). Color of stigma: RHS 4C (Yellow). Color of styles: RHS 151B (Yellow-green).

*Pollination requirements.*—Exemplary cross pollination varieties for fruit set include 'Idared', 'Granny Smith', 'Gala', 'Golden Delicious', 'Golden Hornet', and 'Everest'.

*Fragrance.*—Fresh, soapy clean scent.

*Bloom season (Time of beginning of flowering).*—Early to medium. In 2022, first blossom opened on April 11, full bloom by April 24, and end of blooming by May 2.

Fruit:

*General.*—Measurements are the average of 15 typical 'Nicored' apples. Size: 70-75 mm. Length: Approximately 66 mm. Width: Approximately 73 mm. Shape: Conic, no ribbing or lobes. Calyx eye fully open, shape of calyx tube is waisted, width of eye basin is medium/broad, depth is medium. Basin: Shape: waisted. Width: Approximately 23 mm. Depth: Approximate 6 mm. Cavity: Width: Approximately 23 mm. Depth: Approximately 6 mm. Depth of stalk cavity and width of stalk cavity is medium like 'Golden Delicious'.

*Fruit stem.*—Length: Approximately 17 mm. Diameter: Approximately 2 mm. Color: RHS N144A (Yellow-green). Locules: 5. Length: Approximately 17 mm. Width: Approximately 11 mm.

*Fruit skin.*—Tendency to crack: Some over-mature fruit cracks around the stem. Thickness: Relatively thin. Surface texture: Smooth. Lenticels: Present, about 4 per $cm^2$. Diameter: Approximately 0.4 mm. Color: RHS N155A (White). Color: General color effect: RHS 45B (Red). Ground color RHS 10B (Yellow). Over color: RHS 60B (Red-purple)(with bloom removed). Pattern of over color: Only solid flush. Relative area of over color: Large. Width of fruit stripes: No stripes, only solid flush. Russetting: Absent or very low. Bloom: Absent or very weak.

*Flesh.*—Flavor: 'Nicored' flavor can be described as a blend of a juicy 'Gala' and a tangy-sweet 'Braeburn'. It has a balanced sweet and sour flavor and a crisp texture. ° Brix: Minimum 12, average of 14. Juiciness: Very juicy. Color: RHS 12A (Yellow). Aroma: Full-flavored apple juice with a sweet-sour balance. Firmness: 7-8 $kg/cm^2$ at harvest.

*Core.*—Shape: Elliptical. Diameter: Approximately 35 mm. Number of bundles: Approximately 5 per fruit. Core length: Approximately 30 mm. Calyx tube length: Approximately 12 mm (measured as the length from the calyx end at the point of sepal attachment to the point of calyx tube closure).

*Seed.*—Number: About 2 per cell. Shape: Acute/oval. Length: Approximately 7 mm. Width: Approximately 3 mm. Color: RHS 175A (Greyed-orange).

Figure 9:
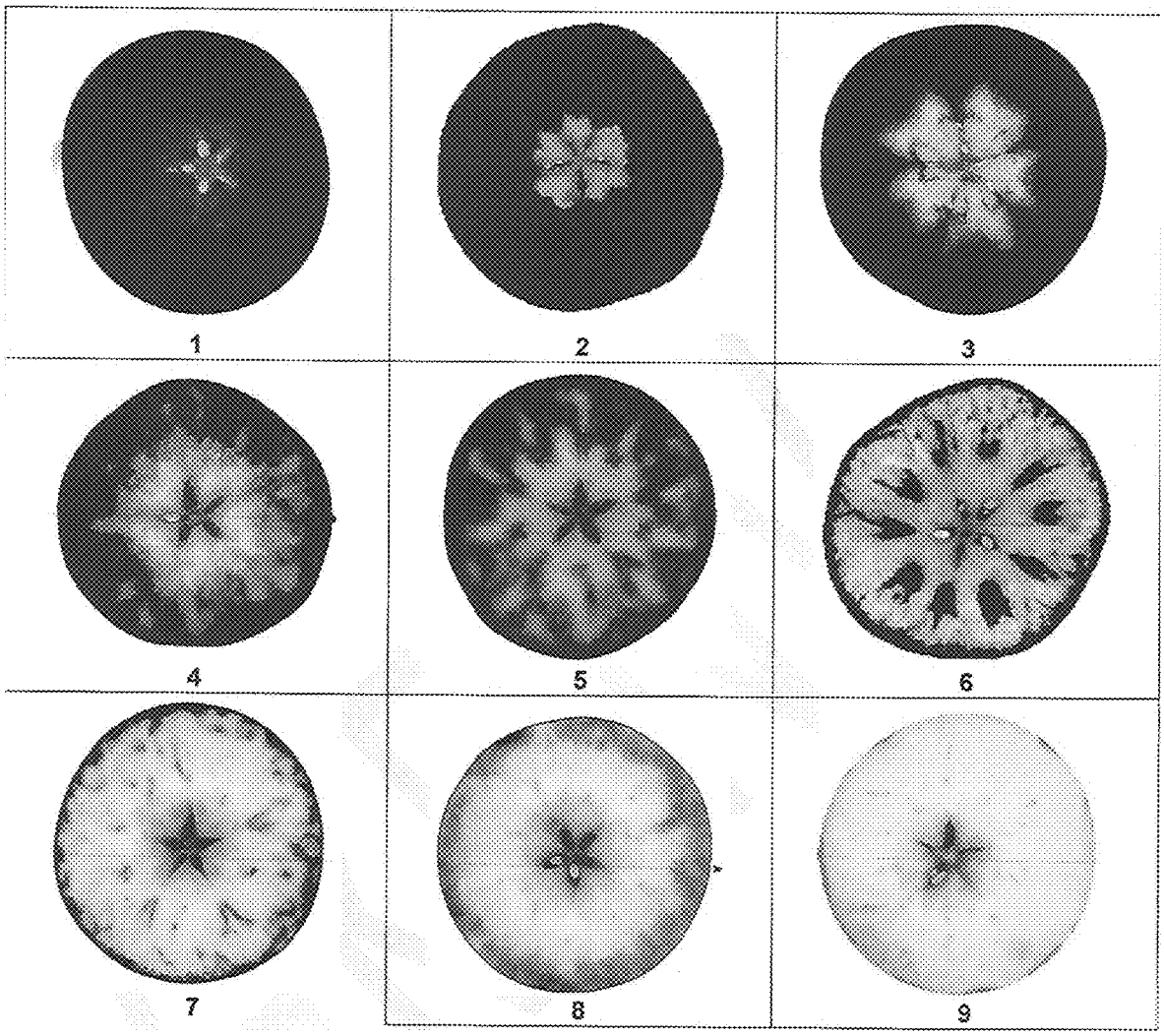
FIG. 9 illustrates the grading scheme used to quantify starch content in fruit.

*Fruit production.*—Fruit should ideally be harvested once fruit has the target parameters below: Average sugar content=12° Brix. Minimum firmness=7 $kg/cm^2$. Streif index (d)=0.11 to 0.19. Minimum starch content=3 to 5.5 (ideally 3-4)(See FIG. 9 for starch measurement scale).

*Time of fruit eating maturity.*—Late. In 2021, optimum harvest time was between September 26 and October 4.

*Usage.*—Fresh market.

*Storage.*—Very good storability under ULO conditions (1° C., 2% $O_2$, $CO_2$) for up to 10 months, 'Nicored' keeps very firm and crispy for about 12-14 days at room temperature.

*Shipping quality of fruit.*—Excellent, not sensitive to bruising.

*Productivity of fruit.*—About 10 kilograms for a 4-year-old tree.

COMPARISON TO PARENTAL AND SIMILAR VARIETIES

'Nicored' differs from its parent and also similar variety 'Nicoter' (U.S. Plant Pat. No. 17,201)(also the source variety of 'Nicored') in that for 'Nicored' the intensity of the fruit over color is dark, the hue of the fruit over color is purple red, the relative area of the fruit over color is large, and the fruit over color is present at 100 days post-bloom, whereas for similar variety 'Nicoter' the intensity of the fruit over color is medium, the hue of the fruit over color is red, the relative area of the fruit over color is medium, and the fruit over color is absent at 100 days post-bloom.

'Nicored' differs from the similar variety 'Gala' (U.S. Plant Pat. No. 3,637) in that the fruit flavor of 'Nicored' has a sweet and sour balance, whereas the fruit flavor of 'Gala' is primarily sweet. In addition, 'Nicored' fruit maintains a firm crispy texture after storage, whereas 'Gala' fruit has a tendency to soften after storage.

What is claimed is:

1. A new and distinct variety of apple tree named 'Nicored' as shown and described herein.

* * * * *